(12) United States Patent
Bosma et al.

(10) Patent No.: US 9,155,281 B2
(45) Date of Patent: Oct. 13, 2015

(54) MILKING PLANT

(75) Inventors: Epke Bosma, Hölö (SE); Nils Erik Holmertz, Huddinge (SE)

(73) Assignee: DELAVAL HOLDING AB, Tumba (SE)

( * ) Notice: Subject to any disclaimer, the term of this patent is extended or adjusted under 35 U.S.C. 154(b) by 1491 days.

(21) Appl. No.: 12/303,326

(22) PCT Filed: May 28, 2007

(86) PCT No.: PCT/SE2007/050362
§ 371 (c)(1),
(2), (4) Date: Jan. 6, 2009

(87) PCT Pub. No.: WO2007/149036
PCT Pub. Date: Dec. 27, 2007

(65) Prior Publication Data
US 2009/0173281 A1 Jul. 9, 2009

(30) Foreign Application Priority Data
Jun. 21, 2006 (SE) ........................ 0601364

(51) Int. Cl.
*A01J 5/00* (2006.01)
*A01J 5/013* (2006.01)
(Continued)

(52) U.S. Cl.
CPC .............. *A01J 5/0131* (2013.01); *A01J 5/045* (2013.01); *G01N 1/2035* (2013.01)

(58) Field of Classification Search
CPC ....... A01J 5/0131; A01J 5/045; G01N 1/2035

USPC ...................... 119/14.01, 14.08, 14.42, 14.46
See application file for complete search history.

(56) References Cited

U.S. PATENT DOCUMENTS

| | | |
|---|---|---|
| 2,047,330 A | 7/1936 | Petersen |
| 3,841,756 A | 10/1974 | Grochowicz |
| 4,437,346 A | 3/1984 | Kummer |

(Continued)

FOREIGN PATENT DOCUMENTS

| | | | |
|---|---|---|---|
| DE | 3222234 A1 * | 12/1983 | ............... G01N 1/10 |
| EP | 0161552 | 11/1985 | |

(Continued)

OTHER PUBLICATIONS

International Search Report dated Sep. 21, 2007, in PCT application.

*Primary Examiner* — Joshua Huson
(74) *Attorney, Agent, or Firm* — Young & Thompson

(57) ABSTRACT

A milking plant includes a milking member to be attached to a teat of an animal to be milked during a milking operation. A milk container is connected to the milking member and adapted to collect the milk extracted during the milking operation. A milk pump, being a part of a milk transport conduit, defines a suction side and a pressure side. A milk tank is connected to the milk container via the milk transport conduit and adapted to collect the milk from the milk container. A milk sample discharge device is connected to the milk transport conduit at the pressure side. The milk pump is adapted to transport during a milk transport operation the milk extracted during the milking operation from the milk container in a major flow to the milk tank and in a minor flow via the milk discharge device.

21 Claims, 3 Drawing Sheets

(51) Int. Cl.
*A01J 5/04* (2006.01)
*G01N 1/20* (2006.01)

(56) References Cited

U.S. PATENT DOCUMENTS

| | | | |
|---|---|---|---|
| 4,966,198 A | | 10/1990 | Hartsone |
| 5,572,946 A | * | 11/1996 | Holroyd .................... 119/14.01 |
| 5,746,153 A | | 5/1998 | Hoefelmayr |
| 5,957,081 A | * | 9/1999 | van der Lely et al. ..... 119/14.09 |
| 7,448,344 B2 | * | 11/2008 | Bosma et al. .............. 119/14.08 |
| 2006/0037541 A1 | * | 2/2006 | Wase et al. ................ 119/14.27 |
| 2007/0113790 A1 | * | 5/2007 | Akerman ................... 119/14.02 |
| 2008/0035063 A1 | * | 2/2008 | Birk et al. ................. 119/14.04 |
| 2008/0276870 A1 | * | 11/2008 | Johannesson et al. ..... 119/14.08 |

FOREIGN PATENT DOCUMENTS

| | | |
|---|---|---|
| EP | 1123651 | 8/2001 |
| EP | 1254595 | 11/2002 |
| WO | 2005020674 | 3/2005 |

* cited by examiner

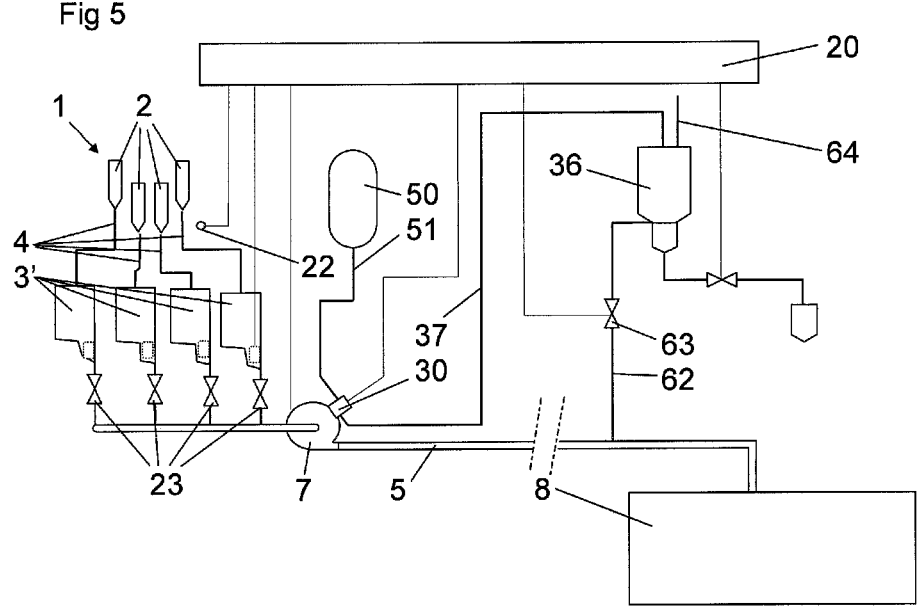

MILKING PLANT

FIELD OF THE INVENTION

The field of the present invention is milking plants.

BACKGROUND OF THE INVENTION AND PRIOR ART

During milking of animals it is important to establish regularly the concentration of fat in the milk. The fat concentration varies during the milking operation, for instance the fat concentration of the milk at the beginning of the milking operation may differ from the fat concentration of the milk at the end of the milking operation. Normally the fat concentration of the milk increases during the milking operation. It is therefore often not satisfactory to take one milk sample at any point of time during the milking operation since the fat concentration of such a milk sample will probably not provide a representative value of the fat concentration of the milk extracted during the milking operation.

Furthermore, the fat is not homogeneously distributed in the milk collected in the milk container, which also makes it difficult to take a representative milk sample from the milk container where the milk extracted during one milking operation is collected. In order to solve this problem, the milk in the milk container can be mixed by means of air before the milk sample is taken. However, such a mixing creates a risk for elevated free fatty acid values (FFA).

EP-B1-1 123 651 discloses several embodiments of a milking plant. One embodiment comprises a milking member to be attached to the teats of an animal to be milked during a milking operation. A milk container is connected to the milking member and adapted to collect the milk extracted during the milking operation. The milk container comprises a measuring chamber which is filled and emptied several times during a milking operation. Pressurised air is supplied to the milk in the measuring chamber. A milk tank is connected to the measuring chamber of the milk container via a milk transport conduit and adapted to collect the milk from the milk container. A milk pump is arranged to transport the milk from the measuring chamber to the milk tank, wherein the milk is transported in separate milk portions from the milk container. The milk pump defines a suction side and a pressure side, and has a constant stroke value, i.e. the milk pump is positive displacement pump. A milk sample discharge device is connected to the pressure side of the milk transport conduit. A milk sample container is connected to the milk sample discharge device, which is adapted to permit discharge of a minor quantity of the milk extracted during the milking operation to the milk sample container.

SUMMARY OF THE INVENTION

The object of the present invention is to remedy the problems mentioned above. More specifically, the object of the present invention is to enable achievement of representative milk sample from the milk collected during one milking operation of an animal. Even more specifically, the object of the present invention is to achieve such a representative milks sample suitable for determining the fat concentration of the milk extracted during one milking operation of an animal. It is also an object of the present invention to prevent carry over of milk from a preceding milking operation in a milk sample of a current milking operation.

This object is achieved by the milking plant initially defined, which is characterised in that the milking plant is arranged to initiate the transport operation at the end of the milking operation.

By means of such a milking plant it is possible to collect all of the milk from one milking operation before the transport of the milk is initiated. The milk sample to be taken may thus be based on this total milk quantity, which means the invention enables the achievement of a representative milk sample reflecting the quality, e.g. the fat content, of the whole milk quantity extracted during one milking operation.

This object is also achieved by the milking plant initially defined, which is characterised in that the milk pump comprises a centrifugal pump.

By means of such a centrifugal pump, it is possible to control the pump in an accurate manner to achieve a minor desired and representative quantity of the milk extracted during a milking operation. The centrifugal pump may thus be arranged to permit, during the transport operation, transportation of the major flow of milk from the at least one milk container to the milk tank and the minor flow of milk through the milk sample discharge device to, for instance, a milk sample container or any other receiving member, such as a test tube, or on-line to any suitable evaluation equipment.

Advantageously, the transportation of the minor flow of milk takes places at least partly simultaneously with the transportation of the main flow of milk. Consequently, the minor flow of milk may be discharged simultaneously with the discharge of the main flow milk, which improves the possibilities to obtain a milk sample representative for the all of the milk extracted during the milking operation.

According to an embodiment of the invention, the milking plant is arranged to initiate the transport operation when the milking operation has been finished.

According to a further embodiment of the invention, the milk sample discharge device defines an inner space communicating via a discharge passage with the milk transport conduit at the pressure side. Advantageously, a filter is provided to filter the milk flowing through the discharge passage. Thus particles and the like may be separated from the minor milk flow and the milk sample.

According to a further embodiment of the invention, the milk pump comprises a pump housing and the milk sample discharge device is connected to the pump housing to communicate with milk transport conduit at the pressure side. Advantageously, the discharge passage is formed by an aperture extending through the pump housing and permitting communication between the pressure side and the inner space of the milk sample discharge device. The pump housing may also define a lower housing part and an upper housing part, adapted to be located above an outlet opening during the milk transport operation, wherein the aperture advantageously may be provided on the upper housing part. By providing the aperture on the upper housing part above the outlet, the milk sample discharge device and any components associated therewith may easily be drained when the milk pump is in a rest position. Furthermore, the milk pump may comprise a rotating pump member arranged in the pump housing.

According to a further embodiment of the invention, the milk sample discharge device defines a milk passage from the pressure side of the milk transport conduit via a milk sample conduit, and comprises a valve mechanism which is arranged to be in one of a primary state, in which the milk passage is closed, and a secondary state, in which the milk passage is opened. By such a valve mechanism, a representative quantity of the milk may be selectively discharged to the milk sample container. Moreover, the valve mechanism makes it possible to transport a determined quantity or volume of milk to the milk sample container. The valve mechanism also makes it possible, for instance, to discharge continuously a minor milk flow during at least a major part of the transportation operation or to discharge the minor milk flow in determined intervals of the transportation operation to the milk sample container. Advantageously, the valve mechanism comprises a valve body provided in the inner space of the milk sample discharge device.

According to a further embodiment of the invention, the milking plant comprises a control unit adapted to control the milk pump and the valve mechanism. Advantageously, the control unit may be adapted to control the milk pump to initiate the milk transport operation and to control the valve mechanism to change from the primary state to the secondary state a certain time interval after the milk transport operation has been initiated. By such a delayed initiating of the minor milk flow, any carry over of milk from a preceding milking operation, collected in the milk transport conduit at the pressure side thereof, to the milk sample container can be avoided.

According to a further embodiment of the invention, the milking comprises a sensor adapted to sense when the milking operation has been finished. By such a sensor, connected to or forming a part of the control unit, the initiating of the transport operation may be performed in an automatic manner.

According to a further embodiment of the invention, the milking plant comprises a milk sample container connected to the milk sample discharge device and adapted to receive the minor flow of milk. Advantageously, the milk passage for the minor flow of milk extends from the pressure side of the milk transport conduit to the milk sample container via the milk sample conduit.

According to a further embodiment of the invention, the milk sample discharge device defines a pressurised gas passage from a pressurised gas source to the milk sample container via the milk sample conduit and wherein the valve mechanism is arranged to keep the pressurised gas passage open in the primary state, and thus to permit application of a pressurised gas to the milks sample container via the milks sample conduit. Consequently, a pressurised gas may be supplied through the milk sample conduit to the milk sample container during the primary state when the milk passage is closed, and thus when there is no minor milk flow from the milk transport conduit to the milk sample container. The pressurised gas will ensure that all milk remaining in the inner space of the milk discharge device and in the milk sample conduit will be transported to the milk sample container, and thus an carry over of milk from one milking operation to a successive milking operation may be avoided.

According to a further embodiment of the invention, the milk transport operation is a substantially continuous transport operation with respect to the main flow of milk. Consequently, all, or substantially all, of the milk extracted during one single milking operation of one animal, which is collected in the milk container, may be continuously discharged from the milk container during one single milk transport operation. Although the major flow of milk is continuous, it should be noted that the minor flow of milk during the transport operation may de divided into one or several milk flow portions.

According to a further embodiment of the invention, the milk container is adapted to receive and keep all milk extracted from one animal during one milking operation.

BRIEF DESCRIPTION OF THE DRAWINGS

The present invention will now be described more closely by means of a description of examples of various embodiments and with reference to the drawings attached hereto.

FIG. 5 discloses a schematic illustration of a milking plant according to a second embodiment of the present invention.

DETAILED DESCRIPTION OF VARIOUS EMBODIMENTS OF THE INVENTION

Figure 1:
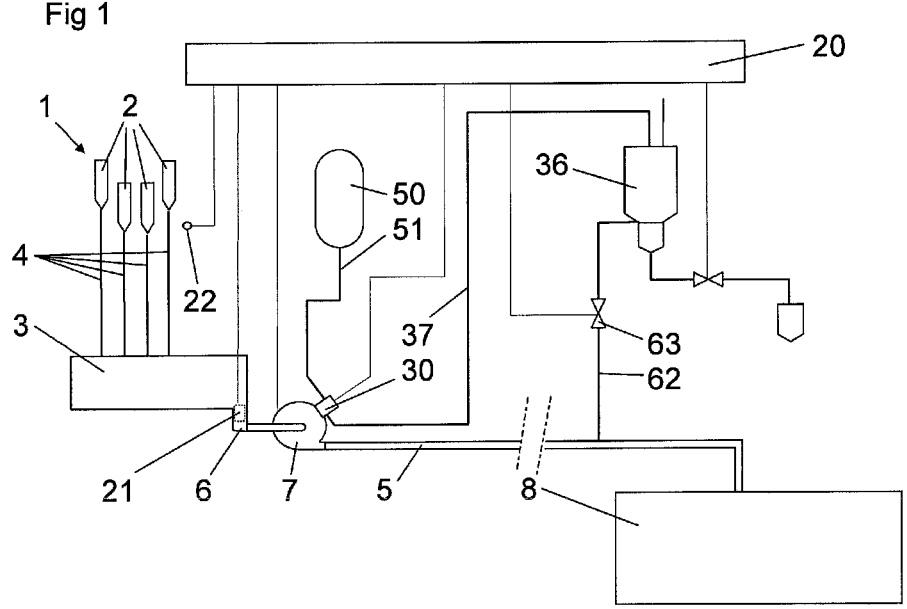
FIG. 1 discloses a schematic illustration of a milking plant according to a first embodiment of the present invention.
Figure 2:
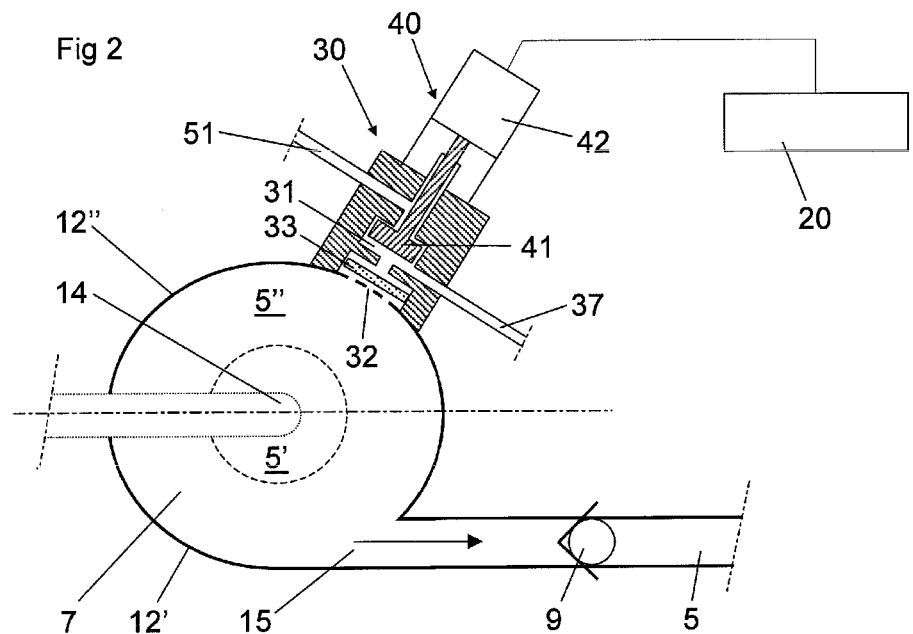
FIG. 2 discloses schematically a partly sectional side view of a milk pump and a milk sample discharge device of the milking plant in FIG. 1.

FIG. 1 discloses schematically a milking plant comprising a milking member 1 having four teat cups 2 to be attached to a respective teat of an animal to be milked. Each teat cup 2 is thus adapted to extract the milk from one udder quarter of the animal. The teat cups 2 may be directly connected to a milk container 3 via a respective milk hose 4, as in the embodiment disclosed, or alternatively via a claw (not disclosed). The milk container 3 is adapted to receive and keep all milk extracted from one animal during one milking operation. The milk container 3 is connected to a milk transport conduit 5 at a container outlet 6. The milk transport conduit 5 includes a milk pump 7 defining a suction side 5' upside the milk pump 7 and a pressure side 5" downstream the milk pump 7, see FIG. 2. The milk transport conduit 5 is connected to a milk tank 8 so that the milk collected in the milk container 3 may be transported via the milk transport conduit 5 and the milk pump 7 to the milk tank 8 during a milk transport operation. The milk transport conduit 5 also comprises a one-way valve 9, see FIG. 2, provided downstream the milk pump 7.

Figure 3:
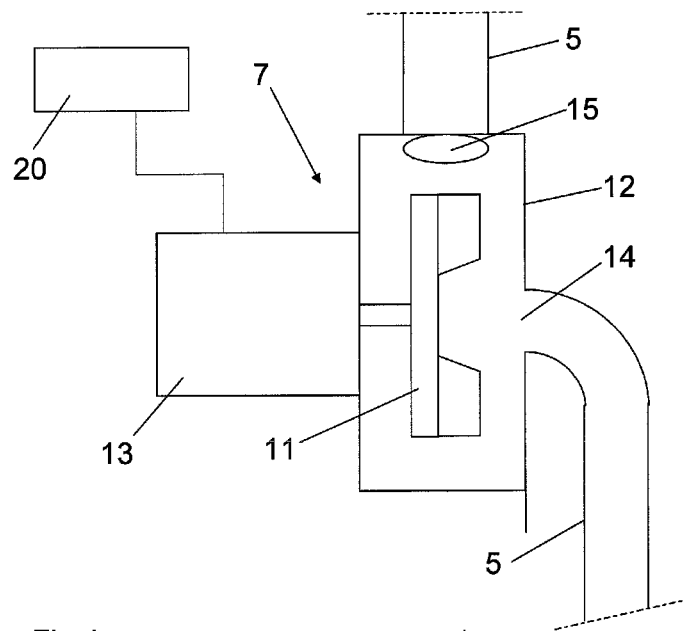
FIG. 3 discloses schematically a partly sectional view from above of the milk pump in FIG. 2.
Figure 4:
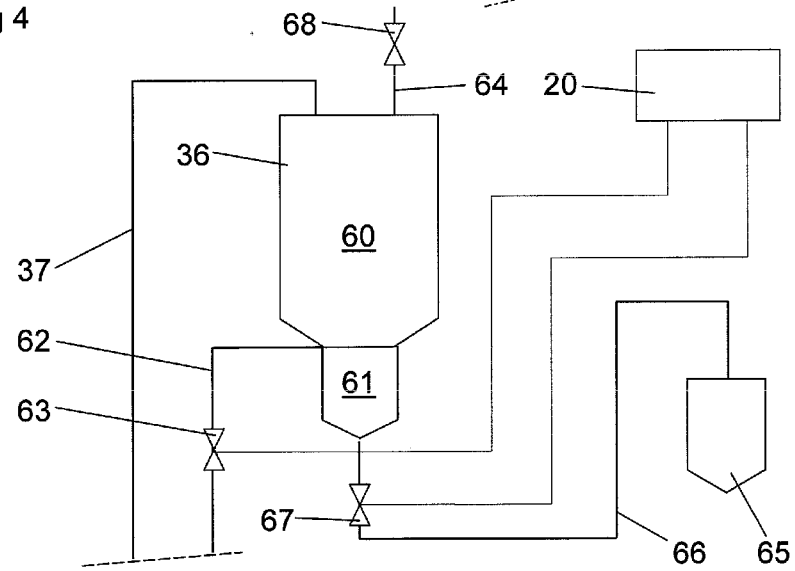
FIG. 4 discloses a milk sample container of the milking plant in FIG. 1.

The milk pump 7 comprises or is constituted by a centrifugal pump, see also FIG. 3. The milk pump 7 comprises a rotating pump member 11 arranged in a pump housing 12. The rotating pump member 11 is driven by any suitable drive motor 13, for instance an electrical, pneumatic or hydraulic motor. The pump housing 12 defines a lower housing part 12' and an upper housing part 12", separated by the dashed-dotted line, see FIG. 2. The pump housing 12 also has an inlet opening 14 of the milk transport conduit 5 and an outlet opening 15 of the milk transport conduit 5. At least the outlet opening 15 is located at the lower housing part 12', at least during the milk transport operation.

The milking plant also comprises a control unit 20 adapted to control the milk pump 7, i.e. the drive motor 13 of the milk pump 7. A first sensor 21 comprising a floating body, is provided in the milk container 3 in the proximity of the container outlet 6 to detect when the milk container 3 is empty or substantially empty. The sensor 21 is connected to the control unit 20. The control unit 20 is adapted to control the drive motor 13 to interrupt the operation of the drive motor 13 when the milk container 3 is empty or substantially empty. A second sensor 22 is provided to sense the milking operation, and in particular to sense when the milking operation has been finished. The second sensor 22 may be connected to or form an integrated part of the control unit 20. The control unit 20 is adapted to initiate the transport operation in response to the second sensor 20, and when the milking operation has been finished.

Furthermore, the milking plant comprises a milk sample discharge device 30 connected to the milk transport conduit 5 at the pressure side 5". In the embodiment disclosed, the milk sample discharge device 30 is connected to and attached directly to the pump housing 12, and more specifically to the upper housing part 12". The milk sample discharge device 30 defines an inner space 31 communicating via a discharge passage 32 with the interior of the milk transport conduit 5, and in the embodiment disclosed with the interior of the pump housing 12. Consequently, the interior of the pump housing 12 may communicate with the inner space 31 of the milk sample discharge device 30 via the discharge passage 32.

The discharge passage 32 is formed by an aperture, or in the embodiment disclosed, by several small apertures, extending through the pump housing 12, and thus permitting the above mentioned communication between the pressure side 5" and the inner space 31 of the milk sample discharge device 30. A filter 33 is provided immediately or substantially immediately outside the apertures in the inner space 31 of the milk sample discharge device 30. The milk sample discharge device 30 is connected to a milk sample container 36 via a milk sample conduit 37. Consequently, the milk sample discharge device 30 defines a milk passage from the pressure side 5" of the milk transport conduit 5 to the milk sample container 36 via the milk sample conduit 37.

The milk pump 7 is thus adapted to transport, during a milk transport operation, the milk extracted during the milking operation from the milk container 3 in a major flow of milk to the milk tank 8 and in a minor flow of milk to the milk sample container 36 via the milk discharge device 30.

The milk sample discharge device 30 also comprises a valve mechanism 40 arranged to be in one of a primary state, in which the milk passage mentioned above is closed, and a secondary state, in which the milk passage is opened. The valve mechanism 40 comprises a valve body 41 which is actuated by an actuator 42 which is connected to the control unit 20. In FIG. 2, the valve mechanism 40 is in the secondary state, i.e. the milk passage is open so that milk may flow from the interior of the milk pump 7 through the discharge passage 32 and the filter 33 in the inner space 31 to the milk sample conduit 37 and the milk sample container 36. The control unit 20 is adapted to control the milk pump 7 to initiate the milk transport operation and to control the valve mechanism 40 to change from the primary state to the secondary state at a certain time interval after the milk transport operation has been initiated. This means that milk from the previous milking operation and remaining in the interior of the pump housing 12 will be pumped away to the milk tank 8 during an initial phase of the milk transport operation. Thereafter, when the valve mechanism 40 has taken the primary state, a minor flow of the milk transported through the milk transport conduit 5 will be separated and discharge through the discharge passage 32 and the filter 33 into the milk sample conduit 37 to the milk sample container 36. It should be noted that the discharge of the minor flow of milk can be controlled by means of the control unit and the valve mechanism 40 to take place, substantially continuously during the remaining part of the milk transport operation, or in several time intervals during the milk transport operation. The valve mechanism 40 may be controlled in such away that a representative quantity of milk is delivered to the milk sample container 36.

The milking plant also comprises a pressurized gas source 50 for the supply of a pressurized gas. The pressurized gas source 50 is connected to the milk sample discharge device 30 via a pressurized gas passage 51.

When the valve mechanism 40 is in the primary state, i.e. when the milk passage is closed, the pressurized gas passage 51 is open to permit the supply of the pressurized gas from the pressurized gas source 50 to the milk sample container 36 via the inner space 31 of the milk sample discharge device 30 and via the milk sample conduit 37. By the application of the pressurized gas, any milk remaining in the milk sample conduit 37 will be transported to the milk sample container 36 so that there will be no milk carried over to the taking of a milk sample during the subsequent milking operation.

The milk sample container 36 comprises an upper main milk-receiving space 60 and a lower sample-receiving space 61. A return conduit 62 extends from the milk sample container 36 back to the milk transport conduit 5. The return conduit 62 is connected to the milk sample container 36 at the border level between the lower sample-receiving space 61 and the upper sample-receiving space 60. A valve 63 is provided on the return conduit 62 and connected to the control unit 20. A conduit is provided to connect the interior of the milk sample container 36 with the surrounding atmosphere, and thus subject the interior of the milk sample container to the atmospheric pressure. The conduit 64 is provided at an upper part of the milk sample container 36. A valve 68 is provided on the conduit 64.

A milk sample receiver 65 is connected to the milk sample container 36 via a milk sample outlet conduit 66. A valve 67 is provided on the milk sample outlet conduit 66 and connected to the control unit 20. The volume of the milk sample receiver 65 is equal, or substantially equal to the volume of the lower sample-receiving space 61.

During the transportation operation, all milk contained in the milk container 3 is transported to the milk sample container 36 as explained above. When all milk has been transported from the milk container 3 to the milk sample container 36, the pressurized gas will be conveyed to the milk sample container 36 providing a stirring action on the milk contained therein. Furthermore, the valve 63 will be opened permitting a major part of the milk in the milk sample container 36, and more specifically the milk contained in the upper main milk-receiving space 60, to be returned to the transport conduit 5, via the return conduit 62, and to the milk tank 8. Thereafter, only the milk contained in the lower sample-receiving space 61 remains in the milk sample container 36. The valve 67 is then opened to permit the milk contained in the lower sample-receiving space 61 to be conveyed to the milk sample receiver 65 via the milk sample outlet conduit 66. The milk in the milk sample receiver 65 will then constitute a representative quantity of the milk contained in the milk container 3 and extracted during one milking operation of one animal. The milk in the milk sample receiver 65 can then be analysed for establishing a representative value of the fat content in the milk.

FIG. 5 discloses a second embodiment which differs from the first embodiment in that the milking plant is adapted to so called quarter milking and comprises four milking members each having a teat cup 2, and four milk containers 3'. Each milk container 3' is connected to a respective one of the teat cups 2 and adapted to collect the milk extracted from a respective one of the udder quarters during the milking operation. In this case, the transport operation may be initiated at the end of the milking operation, for instance when the milking operation has been finished with respect to all of the udder quarters or with respect to 1, 2 or 3 of the udder quarters of the animal. To that end each milk container 3' may comprise a respective first sensor 21 and may be connected to the milk transport conduit 5 via a valve 23, which permits the transport of milk from the milk container 3' when the respective valve 23 has been opened. The valves 23 are connected to the control unit 20 via a connection (not disclosed). The connection of the first sensor 21 to the control unit 20 is disclosed only for one of the first sensors 21.

The volume of milk contained in the milk container 3 or in the milk containers 3, may easily be determined. Thus, the quantity of milk to be transported during the transport operation is known, especially if the transport operation is not initiated until the milking operation has been finished. Since this quantity of milk and the minor flow is known, the valve mechanism 40 may easily be controlled to open and close the milk passage to obtain a milk sample that is representative for the whole quantity of milk extracted during one milking operation.

The present invention is not limited to the embodiments disclosed but may be varied and modified within the scope of the following claims.

The invention claimed is:
1. A milking plant, comprising:
a milking member (1) to be attached to at least one teat of an animal to be milked during a milking operation,
at least one milk container (3, 3') connected to the milking member (1) and adapted to collect the milk extracted during the milking operation,
a milk transport conduit (5) connected to a discharge side of the at least one milk container,
a milk pump (7) being a part of the milk transport conduit (5) and defining a suction side (5') and a pressure side (5"),
a milk tank (8) connected to the at least one milk container via the milk transport conduit (5), including via the milk pump, the milk tank adapted to collect the milk from the at least one milk container, and
a milk sample discharge device (30) connected to the milk transport conduit (5) at the pressure side (5") of said milk pump,
wherein the milk pump (7) is adapted to transport, during a milk transport operation, the milk extracted during the milking operation from the at least one milk container (3, 3') in a major flow to the milk tank and in a minor flow via the milk discharge device (30),
wherein the milking plant is arranged to initiate the transport operation at the end of the milking operation,
wherein the milk pump (7) comprises a pump housing (12), and
wherein the milk sample discharge device (30) is connected to the pump housing (12) to communicate with the milk transport conduit (5) at the pressure side (5").
2. A milking plant according to claim 1, further comprising a system control unit configured to activate the milk pump at the end of the milking operation so that the milk pump transports, during a milk transport operation, the milk extracted during the milking operation from the at least one milk container (3, 3') in a major flow to the milk tank and in a minor flow via the milk discharge device (30).
3. A milking plant according to claim 1, wherein,
the pump housing comprises a discharge passage, and
the milk sample discharge device (30) defines an inner space (31) communicating via the discharge passage (32) with the milk transport conduit at the pressure side.
4. A milk plant according to claim 3,
wherein a filter (33) is provided to filter the milk flowing through the discharge passage (32).
5. A milking plant according to claim 1, wherein the milk sample discharge device (30) defines an inner space (31) communicating via a discharge passage (32), separate from the pump discharge, with the milk transport conduit at the pressure side, and the discharge passage (32) is formed by an aperture extending through the pump housing (12) and permitting communication between the pressure side (5") and the inner space (31) of the milk sample discharge device (30).
6. A milking plant according to claim 5, wherein the pump housing (12) defines a lower housing part (12') and an upper housing part (12") adapted to be located above an outlet opening (15) during the milk transport operation, and wherein the aperture is provided on the upper housing part (12").
7. A milking plant according to claim 6, wherein the milk pump (7) comprises a rotating pump member (11) arranged in the pump housing (12).
8. A milking plant according to claim 1, wherein the milk sample discharge device (30) defines a milk passage for the minor flow of milk from the pressure side (5") of the milk transport conduit (5) via a milk sample conduit (37), and comprises a valve mechanism (40) which is arranged to be in one of a primary state, in which the milk passage is closed, and a secondary state, in which the milk passage is opened.
9. A milking plant according to claim 8, wherein the milk sample discharge device (30) defines an inner space (31) communicating via a discharge passage (32) with the milk transport conduit at the pressure side, and the valve mechanism (40) comprises a valve body (41) provided in the inner space (31) of the milk sample discharge device (30).
10. A milking plant according to claim 8, wherein the milking plant comprises a control unit (20) adapted to control the milk pump (7) and the valve mechanism (40).
11. A milking plant according to claim 10, wherein the control unit (20) is adapted to control the milk pump (7) to initiate the milk transport operation and to control the valve mechanism (40) to change from the primary state to the secondary state a certain time interval after the milk transport operation has been initiated.
12. A milking plant according to claim 10, wherein the plant comprises a sensor (22) adapted to sense when the milking operation has been finished.
13. A milking plant according to claim 1, wherein the milking plant comprises a milk sample container (36) connected to the milk sample discharge device (30) and adapted to receive the minor flow of milk.
14. A milking plant according to claim 13, wherein the milk sample discharge device (30) defines a milk passage for the minor flow of milk from the pressure side (5") of the milk transport conduit (5) via a milk sample conduit (37), and comprises a valve mechanism (40) which is arranged to be in one of a primary state, in which the milk passage is closed, and a secondary state, in which the milk passage is opened, and the milk passage for the minor flow of milk extends from the pressure side (5") of the milk transport conduit (5) to the milk sample container (36) via the milk sample conduit (37).
15. A milking plant according to claim 13, wherein the milk sample discharge device (30) defines a pressurised gas passage (51) from a pressurised gas source (50) to the milk sample container (36) via the milk sample conduit (37) and wherein the valve mechanism (40) is arranged to keep the pressurised gas passage (51) open in the primary state, and thus to permit application of a pressurised gas to the milk sample container (36) via the milk sample conduit (37).
16. A milking plant according to claim 1, wherein the milk transport operation is a substantially continuous transport operation with respect to the main flow of milk.
17. A milking plant according to claim 1, wherein the milk container (3, 3') is adapted to receive and keep all milk extracted from one animal during one milking operation.
18. A milking plant according to claim 1, wherein the milk pump (7) comprises a centrifugal pump.
19. A milking plant, comprising:
a milking member (1) to be attached to at least one teat of an animal to be milked during a milking operation,
at least one milk container (3, 3') connected to the milking member (1) and adapted to collect the milk extracted during the milking operation, a centrifugal milk pump (7) connected to a discharge of the at least one milk container, the centrifugal milk pump having a housing with a pump discharge, a milk transport conduit (5) connected to the pump discharge of the milk pump, a milk tank (8) connected to the milk container via the milk transport conduit (5) and via the milk pump, the milk tank adapted to collect the milk from the at least one milk container, a milk sample discharge device (30) connected to the housing of the milk pump at a location separate from the milk pump discharge, and a system control unit configured to activate the milk pump at the end of the milking operation so that the milk pump transports, during a milk transport operation, the milk extracted during the milking operation from the at least one milk container (3, 3') in a major flow to the milk tank and in a minor flow via the milk discharge device (30).

20. A milking plant, comprising:

a milking member (1) to be attached to at least one teat of an animal to be milked during a milking operation;

a milk container (3, 3') connected to the milking member (1) and adapted to collect the milk extracted during the milking operation of an individual animal;

a centrifugal milk pump (7) connected to a discharge of the milk container, the milk pump having a housing with a pump discharge, the milk pump defining a suction side (5') and a pressure side (5");

a milk transport conduit (5) connected to the pump discharge of the milk pump;

a milk tank (8) connected to the milk container via the milk transport conduit (5) and via the milk pump, the milk tank to collect the milk from the at least one milk container;

a discharge passage (32) on the high pressure side;

a milk sample discharge device (30) connected at the discharge passage, the milk sample discharge device comprising an inner space (31) communicating via the discharge passage (32) with a milk flow from the milk container; and a system control unit configured to activate the milk pump at the end of the milking operation so that the milk pump transports, during a milk transport operation, the milk extracted during the milking operation from the milk container in a major flow to the milk tank and in a minor flow via the milk discharge device (30).

21. The milking plant of claim 20, further comprising:

a milk sample container (36) connected to a discharge of the milk sample discharge device, the milk sample container comprising an upper main milk-receiving space (60) and a lower sample-receiving space (61);

a pressurized gas line connected to the milk sample container, a gas from the pressurized gas line to stir milk collected in the milk sample container;

a valve (63) connected to drain milk collected in the upper main milk-receiving space (60) while leaving milk collected in the lower sample-receiving space (61), the system control unit configured open the valve to permit the milk collected in the upper main milk-receiving space (60), to be drained so that thereafter only the milk contained in the lower sample-receiving space (61) remains in the milk sample container (36); and a milk sample receiver (65) connected to an outlet of the lower sample-receiving space, wherein the milk contained in the lower sample-receiving space is conveyed to the milk sample receiver for analysis for establishing a representative value of the fat content in the milk.

\* \* \* \* \*